(12) United States Patent
Lange et al.

(10) Patent No.: US 7,310,991 B2
(45) Date of Patent: Dec. 25, 2007

(54) EXPLOSION-PROOF GAS SENSOR

(75) Inventors: Björn Lange, Teschow (DE); Nils Haack, Lübeck (DE); Lars Wulf, Sereetz (DE); Rigobert Chrzan, Bad Oldesloe (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 11/244,116

(22) Filed: Oct. 5, 2005

(65) Prior Publication Data

US 2006/0162425 A1 Jul. 27, 2006

(30) Foreign Application Priority Data

Jan. 22, 2005 (DE) .................... 10 2005 003 049

(51) Int. Cl.
*G01N 33/22* (2006.01)
(52) U.S. Cl. ..................................... 73/23.31
(58) Field of Classification Search ............... 73/31.05, 73/23.2, 23.31; 422/94; 356/437
See application file for complete search history.

(56) References Cited

U.S. PATENT DOCUMENTS

| | | | |
|---|---|---|---|
| 4,255,960 A | | 3/1981 | Boutonnat et al. |
| 4,305,724 A | * | 12/1981 | Micko ..................... 436/156 |
| 4,352,099 A | | 9/1982 | Christen et al. |
| 4,466,880 A | * | 8/1984 | Torii et al. ................ 204/428 |
| 4,489,590 A | * | 12/1984 | Hadden ..................... 73/1.04 |
| 4,596,975 A | | 6/1986 | Reddy et al. |
| 4,709,150 A | | 11/1987 | Burough et al. |
| 4,756,885 A | | 7/1988 | Raff et al. |
| 4,822,692 A | * | 4/1989 | Koehler ..................... 428/547 |
| 6,279,376 B1 | * | 8/2001 | Yamada et al. .............. 73/23.2 |
| 6,346,179 B1 | * | 2/2002 | Makino et al. .............. 204/428 |
| 6,453,723 B1 | * | 9/2002 | Ichikawa et al. ............ 73/23.2 |
| 6,469,303 B1 | * | 10/2002 | Sun et al. ................... 250/343 |
| 6,739,177 B2 | * | 5/2004 | Sato et al. .................. 73/23.31 |
| 6,780,298 B2 | * | 8/2004 | Nakamura et al. .......... 204/428 |
| 7,007,543 B2 | * | 3/2006 | Sakawa et al. ............. 73/23.32 |
| 7,034,304 B2 | * | 4/2006 | Tice et al. .................. 250/343 |

FOREIGN PATENT DOCUMENTS

| | | |
|---|---|---|
| DE | 298 23 367 U1 | 6/1999 |
| EP | 0 016 351 A1 | 10/1980 |
| EP | 0 094 863 | 11/1983 |
| EP | 0 182 064 A1 | 5/1986 |
| EP | 0 957 357 A1 | 11/1999 |
| GB | 1 338 870 | 11/1973 |
| GB | 2 262 338 | 6/1993 |
| GB | 2 262 338 A | 6/1993 |
| JP | 2003-227794 | 8/2003 |

* cited by examiner

*Primary Examiner*—Hezron Williams
*Assistant Examiner*—John Fitzgerald
(74) *Attorney, Agent, or Firm*—McGlew and Tuttle, P.C.

(57) ABSTRACT

An explosion-proof gas sensor has a measuring element (2), which generates a measured signal that depends on the concentration of the measured gas and is delimited against the environment by means of a porous, gas-permeable and sintered metal body (7). The sintered metal body (7) has a high mechanical stability, so that the use of additional components, which hinder the diffusion of the gas to be measured into the gas sensor and thus prolong the response time of the gas sensor, can be eliminated.

21 Claims, 1 Drawing Sheet

EXPLOSION-PROOF GAS SENSOR

CROSS REFERENCE TO RELATED APPLICATIONS

This application claims the benefit of priority under 35 U.S.C. § 119 of German Patent Application DE 10 2005 003 049.1 filed Jan. 22, 2005, the entire contents of which are incorporated herein by reference.

FIELD OF THE INVENTION

The present invention pertains to a gas sensor with a measuring element, which generates a measured signal that depends on the concentration of the gas being measured.

BACKGROUND OF THE INVENTION

Examples of such gas sensors are infrared optical gas sensors and catalytic heat tone sensors, which are also used as so-called explosion-proof gas sensors in stationary operation in order to determine combustible gases and the concentration thereof in the ambient air or atmosphere. Within their housings, these gas sensors have a measuring cell, in which the gases to be measured are detected on the basis of physical processes, such as infrared absorption or heat tone. The gas to be measured now enters the gas sensor through openings in the housing or in the measuring cell of the gas sensor, and the response time of the gas sensor to the particular gas to be measured depends on the number and the arrangement of these openings. The larger the number of openings in the housing or in the measuring cell, the more rapidly can the gas to be measured diffuse into the gas sensor. However, there is a risk in case of gas sensors for combustible measured gases such as methane that the gas being measured can be ignited within the measuring cell by heated and electrically operated sensor elements or measuring elements. To prevent the spark generated from spreading into the environment of the sensor, so-called flame traps must be located at the housing openings. These are embodied, in general, by individual sintered metal elements, as they appear, for example, from EP 0 182 064 A1, by which the gas being measured, which is ignited within the measuring cell in the gas sensor, is cooled so intensely during flowing out that the measured gas located outside the gas sensor cannot be ignited. The entire housing construction of the gas sensor must be such that the explosion or flashback protection is still guaranteed even after strong external mechanical effects. The gas sensor housing itself must be manufactured from a mechanically resistant material and, in particular, precautionary measures must be taken to prevent damage to the sintered elements. One possibility of embodiment is the protection by a stable component arranged on the outside, which is permanently attached above the sintered element. One drawback of this solution is the increased manufacturing cost for the gas sensor due to the additional component. On the other hand, the diffusion of the gas to be measured into the measuring cell is compromised by part of the surface of the sintered element being covered, as a result of which the gas sensor will have an undesired, long response time.

An alternative solution for protecting the sintered element is the structural integration in the housing, so that complete flashback protection of the housing is achieved and the sintered element itself cannot be damaged. However, this solution also involves the drawback that the diffusion of the gas to be measured into the measuring cell is more difficult, which is associated with a longer response time of the gas sensor, and that additional components and assembly steps become necessary.

SUMMARY OF THE INVENTION

The object of the present invention is to provide an explosion-proof gas sensor, which has a large surface for the diffusion of the gas to be measured into the gas sensor without additional components and at the same time has high mechanical stability.

According to the invention, a gas sensor is provided with a measuring element, which generates a measured signal that depends on the concentration of the gas being measured. The gas sensor with the measuring element is delimited against the environment by means of a porous, gas-permeable and sintered metal body.

An essential advantage of the present invention is that the measuring cell with the measuring element is entirely delimited by a porous, gas-permeable, sintered metal body against the ambient atmosphere, and the flashback protection against external mechanical effects is assumed entirely by the metal body itself, which is rigidly connected to the base area, without the need to use additional components for stabilization. The sintered metal body also guarantees, besides the desired explosion protection, the desired mechanical protection and offers a large effective surface for a high rate of diffusion of the gas to be measured into the gas sensor, which surface is not reduced by additional components or housing parts.

The metal body may be a hollow cylinder closed on its face. The metal body may be formed of a special steel and may have a wall thickness of 3 mm to 5 mm and a mean pore size of 10 µm to 80 µm and especially 30 µm to 60 µm. The metal body may advantageously be resintered under vacuum at a temperature above 1,200° C. The metal body may be connected to the base area of the gas sensor according to a pulsed current arc welding method.

A replaceable cap made of a porous, gas-permeable and water-impermeable material may be attached to or screwed on the metal body. The cap may be formed of PTFE (polytetrafluoroethylene) or hydrophobized PE (polyethylene), especially a sintered PTFE or PE with a pore volume of about 30% to 70%.

A calibrating adapter having a gas admission connection pipe may be provided for supplying the calibrating gas to the cap of the gas sensor. The calibrating adapter may be attached to or screwed on the cap. The cap and the calibrating adapter may be designed as individual parts or together as a one-piece component.

The gas sensor may be an infrared optical gas sensor in which case the measuring element includes infrared detector. The gas sensor may be a catalytic heat tone sensor with the measuring element including a pellistor.

The cap may have a smaller layer thickness and/or a higher porosity in the area of the gas admission pipe connection than in the rest of the area (the remaining area).

The gas sensor may have a cuvette heater in the area of the gas admission pipe connection of the calibrating adapter.

The cap and the calibrating adapter may be connected to the gas sensor both during the use for measurement and during the calibration.

The flow resistance of the material of the cap may be selected to be such that the pressure in the area of the gas sensor exceeds the dynamic pressure of the wind on the outer side of the cap with the calibrating adapter during the calibration due to the calibrating gas supplied.

Due to the geometry of the calibrating adapter and the flow resistance of the material of the cap, the diffusion of the gas to be measured to the measuring element is hindered only to the extent that the response time of the gas sensor is prolonged by less than 30% during gas measurement compared to the operation without the calibrating adapter.

The flow resistance of the material of the cap is advantageously selected to be such that the overpressure generated by the calibrating gas flow through the gas admission pipe connection does not exceed 50 hPa.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The FIGURE is a sectional view of an infrared optical gas sensor according to an exemplary embodiment of the present invention.

DESCRIPTION OF THE PREFERRED EMBODIMENTS

Figure 1:
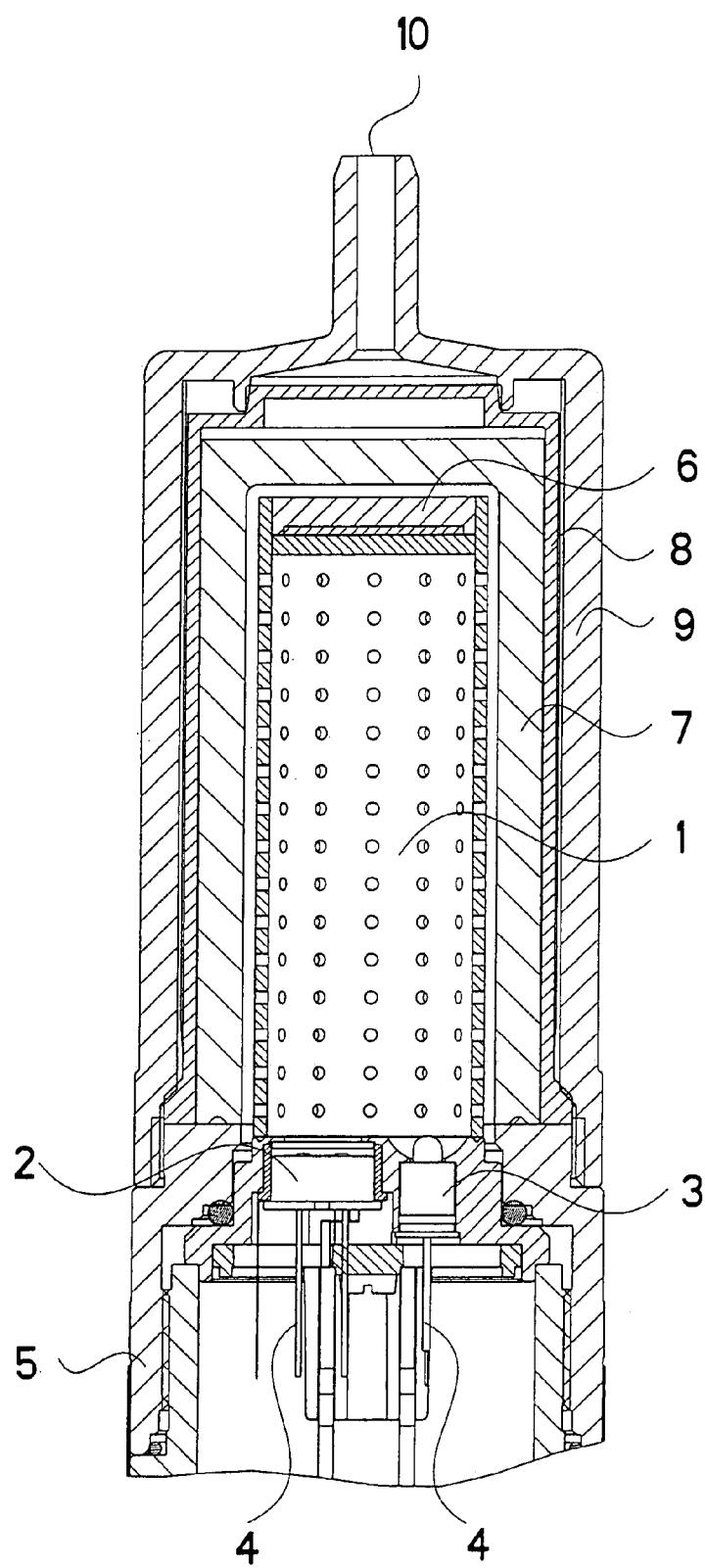

Referring to the drawings in particular, the gas sensor shown is an infrared optical gas sensor with a radiation source 3 and with a measuring element 2, which is designed as an infrared detector and is arranged in the base area 5 of the gas sensor, which is manufactured from a metal or a plastic. The electric contacts 4 are connected to an electronic evaluating unit of the gas sensor, which joins the base area 5. The measuring cell, which is designed as a cylindrical measuring gas cuvette 1 here, has a radiation-reflecting design on the inside in the case of the infrared optical gas sensor and has perforations, which are distributed over the jacket surface and make possible the diffusion of the gas, whose concentration is to be measured, into the cuvette. Such a gas sensor is, for example, a gas sensor installed stationarily at a certain measuring site, which may be poorly accessible, as it is used, for example, in industrial and process plants in the chemical or petroleum/natural gas industry. The gas sensor shown is rigidly connected to the base area 5 by an especially cylindrical, porous, gas-permeable, sintered metal body 7 acting as an explosion protection according to a pulsed current arc welding method, so that explosion of the possibly explosive gases present in the environment cannot be triggered by possible electric sparks in the gas sensor. The metal body 7 consists of a sintered, porous and gas-permeable special steel with a wall thickness of 3 mm to 4 mm and a mean pore size of 10 µm to 80 µm and especially 30 µm to 60 µm. Experiments have revealed that the explosion protection, the mechanical stability and the diffusion properties are especially favorable if the sintered metal body 7 is subjected to resintering under vacuum at a temperature exceeding 1,200° C. Moisture effects and errors of measurement due to condensation in the gas sensor are prevented from occurring with the electric heater 6.

A replaceable, likewise cylindrical cap 8 made of a porous, gas-permeable and water-impermeable material is attached to or screwed on the porous, sintered metal body 7. The cap 8 is preferably made of a sintered PTFE or sintered, hydrophobized PE (polyethylene) with a pore volume of about 30% to 70% and a layer thickness of, e.g., about one mm, the color ranging from light to white. Due to the light color of the material of the cap 8 the state of consumption is clearly visible for a possible replacement after a corresponding exposure to dust and environmental effects. The porous hydrophobic material of the cap 8, especially PTFE or PE, ensures that no moisture will penetrate into the gas sensor or the metal body 7 and these will not consequently be damaged or their measuring function will not be compromised by moisture.

A calibrating adapter 9 which is manufactured, for example, from a glass fiber-reinforced plastic such as polyacryl, and is screwed on the gas sensor, is located above the metal body 7 with the cap 8. The calibrating adapter 9 is manufactured with perforations in order to hinder the diffusion of the gas from the environment as little as possible, and it has a gas admission pipe connection 10 for the connection of a calibrating gas supply line from a pressurized gas container, for example, a pressurized gas cylinder for calibrating gas. The calibrating adapter 9 preferably remains on the gas sensor both during the measurement and during the calibration, so that when the calibrating gas storage container is connected to the gas admission gas connection 10, remote calibration is readily possible when needed by opening the calibrating gas storage container, but without mounting effort being necessary for changeover for each calibration as before. This is especially advantageous at poorly accessible measuring sites.

The flow resistance of the porous material of the cap 8 is selected by selecting the layer thickness and/or the porosity such that the pressure in the measuring cell exceeds the dynamic pressure of the wind on the outer side of the cap 8 with the calibrating adapter 9 attached during the calibration due to calibrating gas admitted via the gas admission pipe connection 10, so that the calibration is not affected by wind.

The cap 8 is preferably provided with a smaller layer thickness and/or with a higher porosity in the area of the gas admission pipe connection 10 than in the rest of the area in order to make possible the entry of the calibrating gas into the interior space of the cap 8 as unhindered as possible, so that the lowest possible calibrating gas pressure is needed. The calibrating adapter 9 is designed in the area of the gas admission pipe connection 10 in the upper section of the cap 8 in the form of, e.g., a base section such that good sealing of the area in which the calibrating gas flows into the cap 8 is ensured. The rest of the area of the cap 8 is selected to be such that an overpressure, which at least corresponds to the dynamic pressure of the maximum tolerable external wind speed during the calibration operation, is generated in the measuring cell in case of a calibrating gas flow rate of, e.g., 1 L/minute, so that the calibration is not affected in an unacceptable manner. On the other hand, the incoming flow of the gas to be measured through the cap 8 shall be as unhindered as possible during the rest of the measuring time with the calibrating adapter 9 screwed on. The pressure build-up at the material of the cap 8, through which the gas flows, is proportional to the calibrating gas flow, but inversely proportional to the conductance of the air and to the value of the area through which the flow takes place. It was determined that in case of acceptable calibrating gas flow rates of about 1 L/minute, the conductance of the air L equals about $$100 \frac{mL}{s \cdot cm^2 \cdot bar}$$

in case of a remaining surface totaling about 45 cm² outside the area in which the calibrating gas flows in and a desired pressure build-up of 4 hPa.

While a specific embodiment of the invention has been shown and described in detail to illustrate the application of the principles of the invention, it will be understood that the invention may be embodied otherwise without departing from such principles.

What is claimed is:

1. A gas sensor, comprising:
   a measuring element, which generates a measured signal that depends on the concentration of the gas being measured;
   a porous, gas-permeable and sintered cylindrical metal body having an interior and top wall and a side wall defining a gas radial flow path, whereby gas passes through said top wall in an axial direction and gas passes through said side wall in a radial direction, said measuring element being mounted exposed only to said interior and being separated from the environment by said sintered metal body, said metal body being resintered under vacuum at a temperature above 1200° C.; and
   a cap having a gas permeable top portion and at least one gas permeable side portion, whereby gas passes through said top portion in an axial direction and said gas passes through said at least one side portion in a radial direction, said cap being attached to said metal body.

2. A gas sensor in accordance with claim 1, wherein the metal body is formed of steel and has a wall thickness of 3 mm to 5 mm and a mean pore size of 10 μm to 80 μm.

3. A gas sensor in accordance with claim 1, wherein the metal body has a wall thickness of 3 mm to 5 mm and a mean pore size of 30 μm to 60 μm.

4. A gas sensor in accordance with claim 1, wherein the metal body is connected to the base area of the gas sensor according to a pulsed current arc welding method.

5. A gas sensor in accordance with claim 1, wherein the cap is formed of a sintered PTFE (polytetrafluoroethylene) or hydrophobized PE (polyethylene) with a pore volume of about 30% to 70%.

6. A gas sensor in accordance with claim 1, wherein the gas sensor is an infrared optical gas sensor and said measuring element comprises an infrared detector.

7. A gas sensor in accordance with claim 1, wherein the gas sensor is a catalytic heat tone sensor and said measuring element comprises a pellistor.

8. A gas sensor in accordance with claim 1, wherein the metal body is a hollow cylinder closed on a face.

9. A gas sensor in accordance with claim 8, further comprising a calibrating adapter having a gas admission connection pipe for supplying a calibrating gas to said cap, said calibrating adapter being attached to said cap.

10. A gas sensor in accordance with claim 1, wherein the cap consists of PTFE (polytetrafluoroethylene) or hydrophobized PE (polyethylene).

11. A gas sensor in accordance with claim 10, wherein the flow resistance of the material of said cap is selected to be such that the overpressure generated by the calibrating gas flow through said gas admission pipe connection does not exceed 50 hPa.

12. A gas sensor in accordance with claim 1, further comprising a calibrating adapter having a gas admission connection pipe for supplying a calibrating gas to the cap, said calibrating adapter being attached to or screwed on said cap.

13. A gas sensor in accordance with claim 12, wherein said cap and said calibrating adapter are one of separate individual parts or an integral one-piece component.

14. A gas sensor in accordance with claim 12, wherein said cap has a smaller layer thickness and/or a higher porosity in the area of said gas admission connection pipe than in a remaining area.

15. A gas sensor in accordance with claim 12, further comprising a cuvette defining a gas measuring space and a cuvette heater in an area of said gas admission pipe connection of said calibrating adapter.

16. A gas sensor in accordance with claim 12, wherein said cap and said calibrating adapter are connected to the gas sensor both during the use for measurement and during the calibration.

17. A gas sensor in accordance with claim 12, wherein the flow resistance of the material of said cap is selected to be such that the pressure in the gas sensor exceeds the dynamic pressure of wind impinging on an outer side of said cap with the calibrating adapter during the calibration due to the calibrating gas supplied.

18. A gas sensor in accordance with claim 12, wherein due to the geometry of said calibrating adapter and the flow resistance of the material of said cap, the diffusion of the gas to be measured to the measuring element is hindered only to the extent that the response time of the gas sensor is prolonged by less than 30% during gas measurement compared to the operation without said calibrating adapter.

19. A gas sensor comprising:
   a cuvette defining a gas measuring space with openings, passages or a gas permeable surface for entry of gas to be measured, whereby gas enters said cuvette in an axial direction and a radial direction;
   a measuring element for measuring gas in the gas measuring space to generate a measured signal that depends on the concentration of the gas being measured; and
   a porous, gas-permeable and sintered metal body having a top portion and at least one side portion, gas passing through said top portion in an axial direction, gas passing through said at least one side portion in a radial direction, said sintered metal body defining a barrier between said cuvette with said measuring element and an environment of the gas sensor, wherein said sintered metal body is resintered under vacuum at a temperature above 1,200° C.;
   a gas-permeable cap mounted to said metal body, said cap surrounding said metal body top portion and said at least one metal body side portion, whereby gas passes through said cap in an axial direction and a radial direction.

20. A gas sensor, comprising:
   a measuring element, which generates a measured signal that depends on the concentration of the gas being measured;
   a porous, gas-permeable and sintered metal body, the gas sensor with said measuring element being separated from the environment by said sintered metal body, said metal body being resintered under vacuum at a temperature above 1200° C.;
   a cap made of a porous, gas-permeable material, said cap being attached to said metal body;
   a calibrating adapter having a gas admission connection pipe for supplying a calibrating gas to said cap, said calibrating adapter being attached to said cap, said cap having a smaller layer thickness and/or a higher porosity in an area of said gas admission connection pipe than in a remaining area.

21. A gas sensor, comprising:

a measuring element, which generates a measured signal that depends on the concentration of the gas being measured; and a porous, gas-permeable and sintered metal body, the gas sensor with said measuring element being separated from the environment by said sintered metal body, said metal body being resintered under vacuum at a temperature above 1200° C.;

a cap attached to said metal body, said cap being composed of a porous, gas permeable material;

a calibrating adapter having a gas admission connection pipe for supplying a calibrating gas to said cap, said calibrating adapter being attached to said cap;

a cuvette defining a gas measuring space; and a cuvette heater located in an area of said gas admission pipe connection of said calibrating adapter.

* * * * *